United States Patent
Cobb et al.

(10) Patent No.: US 11,104,725 B2
(45) Date of Patent: Aug. 31, 2021

(54) AMYLOID BETA OLIGOMER SPECIFIC BINDING MOLECULE

(71) Applicant: DegenRx B.V., Tilburg (NL)

(72) Inventors: Samantha Kathleen Cobb, Melbourne (AU); Michael Foley, Melbourne (AU); Augustinus Petrus Henricus Scheefhals, Tilburg (NL); Armand Wilbrandt Jannes Wichert Tepper, Tilburg (NL)

(73) Assignee: DegenRx B.V., Tilburg (NL)

( * ) Notice: Subject to any disclaimer, the term of this patent is extended or adjusted under 35 U.S.C. 154(b) by 0 days.

(21) Appl. No.: 16/347,927

(22) PCT Filed: Nov. 7, 2017

(86) PCT No.: PCT/NL2017/050719
§ 371 (c)(1),
(2) Date: May 7, 2019

(87) PCT Pub. No.: WO2018/084712
PCT Pub. Date: May 11, 2018

(65) Prior Publication Data
US 2019/0292247 A1   Sep. 26, 2019

(30) Foreign Application Priority Data
Nov. 7, 2016 (NL) .................................... 2017731

(51) Int. Cl.
*C07K 16/18* (2006.01)
*C12N 15/86* (2006.01)

(52) U.S. Cl.
CPC .............. *C07K 16/18* (2013.01); *C12N 15/86* (2013.01); *C07K 2317/20* (2013.01); *C07K 2317/567* (2013.01); *C07K 2317/569* (2013.01); *C07K 2317/92* (2013.01)

(58) Field of Classification Search
CPC ................ C07K 16/18; C07K 2317/20; C07K 2317/567; C07K 2317/569; C07K 2317/92
See application file for complete search history.

(56) References Cited

FOREIGN PATENT DOCUMENTS

| WO | WO-2009033743 A1 * | 3/2009 | ............... A61P 25/28 |
|---|---|---|---|
| WO | 2010/053788 | 5/2010 | |
| WO | 2016/120843 | 8/2016 | |

OTHER PUBLICATIONS

Paul W. E. Fundamental Immunology, 3rd edition, 1993, pp. 292-295.*
Rudikoff et al. Single amino acid substitution altering antigen-binding specificity. Proc Natl Acad Sci USA. Mar. 1982;79(6):1979-83.*
Casset et al. A peptide mimetic of an anti-CD4 monoclonal antibody by rational design. Biochem Biophys Res Commun. Jul. 18, 2003;307(1):198-205.*
Vajdos et al. Comprehensive functional maps of the antigen-binding site of an anti-ErbB2 antibody obtained with shotgun scanning mutagenesis. J Mol Biol. Jul. 5, 2002;320(2):415-28.*
Cheong et al. Diagnostic and therapeutic potential of shark variable new antigen receptor (VNAR) single domain antibody. International Journal of Biological Macromolecules. vol. 147, Mar. 15, 2020, pp. 369-375.*
Kasturirangan, Srinath et al. "Nanobody specific for oligomeric beta-amyloid stabilizes nontoxic form" Neurobiology of Aging, vol. 33, No. 7, Jul. 1, 2012, pp. 1320-1328.
Brannstrom, K. et al. "A Generic Method for Design of Oligomer-Specific Antibodies" PLOS One, vol. 9, No. 3, Mar. 11, 2014, p. e90857.
Lafaye, P. "Single-domain antibodies recognize selectively small oligomeric forms of amyloid beta, prevent Abeta-induced neurotoxicity and inhibit fibril formation".
Pain, Coralie et al. "Camelid single-domain antibody fragments: Uses and prospects to investigate protein misfolding and aggregation, and to treat diseases associated with these phenomena" Biochimie, vol. 111, Feb. 3, 2015, pp. 82-106.
Crisostomo, Amanda C. et al. "Kinetic analysis of IgG antibodies to beta-amyloid oligomers with surface plasmon resonance" Analytical Biochemistry, vol. 481, Apr. 25, 2015, pp. 43-54.

* cited by examiner

Primary Examiner — Gregory S Emch
(74) Attorney, Agent, or Firm — Casimir Jones, S.C.; Robert A. Goetz

(57) ABSTRACT

This disclosure relates to an amyloid beta peptide (Aβ)-oligomer-specific antigen binding molecule and the use thereof as a diagnostic agent or as a therapeutic agent for the treatment or prevention of Alzheimer's Disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, or Gaucher's disease.

19 Claims, 6 Drawing Sheets

Specification includes a Sequence Listing.

Fig.5 —continued—
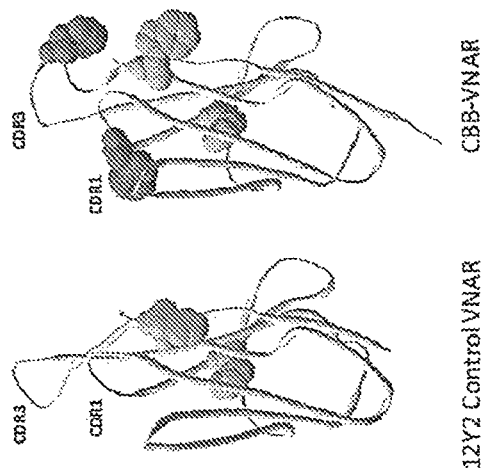
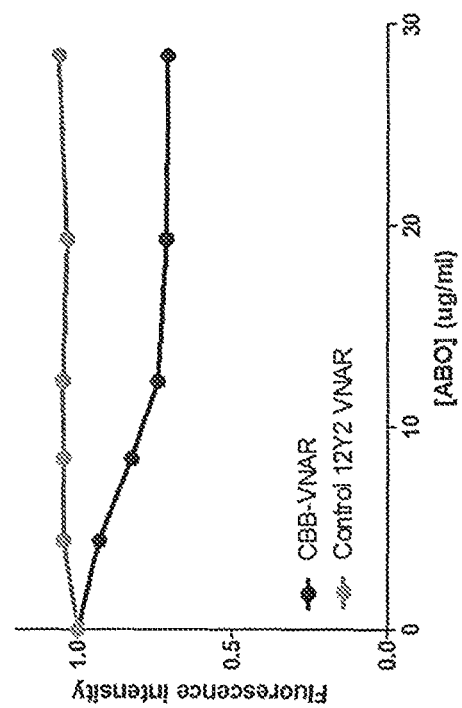

AMYLOID BETA OLIGOMER SPECIFIC BINDING MOLECULE

FIELD OF THE INVENTION

The present invention is in the field of neurodegenerative disorders, and in particular relates to conditions having a beta-amyloid component, including Alzheimer's disease (AD), Vascular Dementia (VD), dementia, pre-dementia, Cognitive Dysfunction Syndrome (CDS) and loss of cognition, in humans and in non-human animals.

BACKGROUND OF THE INVENTION

Alzheimer's disease (AD) is characterized clinically by a progressive and gradual decline in cognitive function. Neuropathologically AD is characterized by the presence of neuropil threads, specific neuron loss, and synapse loss in addition to the hallmark findings of neurofibriallary tangles and senile plaques. Standard measures of pathology refer to the density of neuritic amyloid plaques in affected brain regions. The presence of neuritic plaques composed (in large part) of highly insoluble amyloid beta (Aβ) peptide in the brain parenchyma is required for a diagnosis of AD.

Amyloid beta (Aβ) denotes peptides of typically 36-43 amino acids that are crucially involved in Alzheimer's disease as the main component of the amyloid plaques found in the brains of Alzheimer patients. The peptides result from the amyloid precursor protein (APP), which is cleaved by beta secretase and gamma secretase to yield Aβ. Aβ molecules can aggregate to form soluble oligomers which may exist in several forms. It has been shown that certain oligomers can induce several pathological mechanisms including long-term potentiation (LTP) inhibition, synaptotoxicity, excitotoxicity, cytotoxicity, tau phosphorylation, and inhibition of neurite outgrowth. At least part of these effects are postulated to occur through interactions of Aβ oligomers with cellular receptors (Benilova et al. 2012. *Nature Neuroscience*, 15(3), 349-57).

Aβ oligomer levels in cerebrospinal fluid (CSF) appear to correlate with disease severity and progression. However, hitherto no validated oligomer biomarkers assays for AD diagnosis and/or disease monitoring are currently available. Since Aβ oligomers in solution are in equilibrium with fibrils and monomers, oligomer preparations generally contain a mixture of different species (see FIG. 1) that each may or may not contribute to disease pathology, and may or may not contribute to a measured assay signal. Additionally, the composition of such oligomer preparations differ in time and depend on the experimental conditions employed. In CSF, amyloid beta monomer levels are reported to be 1,000 to 10,000 fold higher than the levels of amyloid beta oligomer (~10 ng/ml monomer vs 1-10 pg/ml oligomer) (Savage et al., 2014. The Journal of Neuroscience: The Official Journal of the Society for Neuroscience, 34(8):2884-97). Therefore, an assay that selectively measures Aβ oligomers in a CSF sample must have exceptional selectivity for Aβ oligomers over monomers, and preferably also over Aβ fibrils.

Additionally, Aβ oligomers may be specifically targeted by therapeutic monoclonal antibodies to treat AD (see, e.g., U.S. Pat. Nos. 7,811,563, 7,780,963, and 7,731,962). Monoclonal antibodies have revolutionized biotechnology and are now key therapeutic drugs in the treatment of human disease. Despite their successes, therapeutic monoclonal antibodies have certain limitations, such as restricted activity against certain types of antigen, poor tissue penetration, unwanted effector function in many situations, the cost of manufacturing, product instability and aggregation. Single domain antibodies that occur naturally in the shark have potential for the development of next generation biotherapeutics. VNARs are small (12 kDa), stable, soluble, monomeric antigen-binding domains that can be configured into many different therapeutic modalities. The isolation of various VNAR based binding moieties has been described. See, e.g., WO2003/014161 and WO2005/118629.

It is an object of the present invention to provide a binding molecule, preferably a single domain binding molecule, that specifically binds to an epitope specific for amyloid beta oligomer, i.e., a conformational epitope, preferably with high affinity, and that preferably does not bind amyloid beta monomers and/or amyloid beta fibrils such as occur in amyloid beta plaques. Such binding molecule may useful for selectively detecting amyloid beta oligomers, e.g., in cerebrospinal fluid, for example for diagnosing AD or assessing AD disease progression upon treatment. Such binding molecule may also be useful as a therapeutic molecule, e.g., to treat AD and other conditions having a beta-amyloid component, including Vascular Dementia (VD), dementia, pre-dementia, Cognitive Dysfunction Syndrome (CDS) and loss of cognition, in humans and in non-human animals.

SUMMARY OF THE INVENTION

The present disclosure relates to an amyloid beta peptide (Aβ)-oligomer-specific antigen binding molecule displaying the following characteristics:
  an affinity for Aβ-oligomers of less than 1 nM; and
  an at least 50-fold greater specificity for Aβ-oligomers than for Aβ-fibrils.

In a further aspect, the present disclosure provides an amyloid beta peptide (Aβ)-oligomer-specific antigen binding molecule comprising an amino acid sequence comprising the structure X-CDR1-Y-CDR3-Z;
in which:
  CDR1 comprises the amino acid sequence of amino acid residues 27-32 of SEQ ID NO:1 (QNGWSR) or an amino acid sequence having at least 50% sequence identity to the amino acid sequence of amino acid residues 27-32 of SEQ ID NO:1; and
  CDR3 comprises the amino acid sequence of amino acid residues 85-102 of SEQ ID NO:1 (LLNPRREEFWFSRRYPVV) or an amino acid sequence having at least 50% sequence identity to the amino acid sequence of amino acid residues 85-102 of SEQ ID NO:1.

```
QNGWSR
is also referred to as SEQ ID NO: 5.

LLNPRREEFWFSRRYPVV
is also referred to as SEQ ID NO: 6.
```

In an embodiment, X represents Framework Region (FW) 1, Y represents FW2-Hypervariable Region 2 (HV2)-FW3a-HV4-FW3a, and Z represents FW4.

In an embodiment, X comprises an amino acid sequence having at least 50% sequence identity to the amino acid sequence of amino acid residues 1-26 of SEQ ID NO:1; Y comprises an amino acid sequence having at least 50% sequence identity to the amino acid sequence of amino acid residues 33-84 of SEQ ID NO:1; and/or Z comprises an amino acid sequence having at least 50% sequence identity to the amino acid sequence of amino acid residues 103-115 of SEQ ID NO:1.

In an embodiment, the antigen binding molecule taught herein comprises the amino acid sequence of SEQ ID NO:1, or an amino acid sequence having at least 50% sequence identity to the amino acid sequence of SEQ ID NO:1.

In an embodiment, the antigen binding molecule taught herein comprises the amino acid sequence of SEQ ID NO:1, except for the last three amino acid residues (alanine-alanine-alanine). In an embodiment, the antigen binding molecule taught herein comprises the amino acid sequence (with CDR 1 and CDR 3 underlined):

AWVDQTPRTATKETGESLTINCVLRDQNGWSRTGWYRTKLGSTNEQSISI
GGRYVETVNKGSKSFSLRISDLRVEDSGTYKCQALLNPRREEFWFSRRYP
VVKGAGTALTVK.

Thus, when reference is made to amino acids 103-115, this skilled person will now understand that reference this also is intended to refer to amino acids 103-112 (i.e. wherein the last three amino acids alanine-alanine-alanine are not present). In an embodiment, X comprises an amino acid sequence having at least 50% sequence identity to the amino acid sequence of amino acid residues 1-26 of SEQ ID NO:2; Y comprises an amino acid sequence having at least 50% sequence identity to the amino acid sequence of amino acid residues 33-79 of SEQ ID NO:2; and/or Z comprises an amino acid sequence having at least 50% sequence identity to the amino acid sequence of amino acid residues 88-97 of SEQ ID NO:2.

The disclosure further provides a nucleic acid molecule encoding the Aβ-oligomer-specific antigen binding molecule taught herein, an expression vector comprising such nucleic acid molecule, and a host cell comprising such nucleic acid molecule or such expression vector.

Preferably the expression vector as taught herein is an AAV viral vector. Therefore, also provided is for a AAV viral vector comprising a nucleic acid molecule encoding the Aβ-oligomer-specific antigen binding molecule taught herein, preferably wherein the AAV vector is an AAV5 vector.

In another aspect, the disclosure teaches a conjugate comprising an Aβ-oligomer-specific antigen binding molecule as taught herein and one or more agents, as well as a multimer comprising two or more Aβ-oligomer-specific antigen binding molecules or conjugates as taught herein.

Further, a pharmaceutical composition comprising the Aβ-oligomer-specific antigen binding molecule or the conjugate or the multimer or the expression vector, preferably AAV viral vector as taught herein and an acceptable carrier is provided.

The Aβ-oligomer-specific antigen binding molecule or conjugate or multimer or expression vector, preferably AAV viral vector as taught herein may be used as a medicament, particularly for use in the treatment or prevention of neurodegenerative diseases, such as for use in the treatment or prevention of Alzheimer's Disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, or Gaucher's disease.

Further, a method of reducing Aβ-oligomer levels in a subject is taught, said method comprising the step of administering to said subject the Aβ-oligomer-specific antigen binding molecule or conjugate or multimer or expression vector, preferably AAV viral vector as taught herein.

Additionally, the disclosure relates to a method of measuring Aβ-oligomer levels in a test sample, said method comprising the steps of:
(a) contacting a test sample with an Aβ-oligomer-specific antigen binding molecule or conjugate or multimer as taught herein under conditions sufficient to form a binding molecule or conjugate or multimer/Aβ-oligomer complex; and
(b) detecting the binding molecule or conjugate or multimer/Aβ-oligomer complex.

Said method may be for diagnosing a subject suffering from a neurodegenerative disease, e.g., selected from the group consisting of Alzheimer's Disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, and Gaucher's disease.

The invention further pertains to a method of assessing disease progression in a subject being treated for a neurodegenerative disease comprising the steps of:
(a) contacting a first test sample taken at a first time point with an Aβ-oligomer-specific antigen binding molecule or conjugate or multimer as taught herein under conditions sufficient to form a binding molecule or conjugate or multimer/Aβ-oligomer complex and detecting the level of binding molecule or conjugate or multimer/Aβ-oligomer complex;
(b) contacting a second test sample taken at a second time point with an Aβ-oligomer-specific antigen binding molecule or conjugate or multimer as taught herein under conditions sufficient to form a binding molecule or conjugate or multimer/Aβ-oligomer complex and detecting the level of binding molecule or conjugate or multimer/Aβ-oligomer complex; and
(c) comparing the level of binding molecule or conjugate or multimer/Aβ-oligomer complex of the first test sample to the level of binding molecule or conjugate or multimer/Aβ-oligomer complex of the second test sample.

In an embodiment, an increased level of binding molecule or conjugate or multimer/Aβ-oligomer complex in the second test sample compared to that in the first test sample is indicative of progression of said neurodegenerative disease in the subject.

In an embodiment, a decreased level of binding molecule or conjugate or multimer/Aβ-oligomer complex in the second test sample compared to that in the first test sample is indicative of effectiveness of the treatment of said neurodegenerative disease in the subject.

In an embodiment, the neurodegenerative disease is selected from the group consisting of Alzheimer's Disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, and Gaucher's disease.

Finally, the present disclosure provides a kit suitable for detecting Aβ-oligomers, comprising the Aβ-oligomer-specific antigen binding molecule or conjugate or multimer as taught herein.

Definitions

Unless otherwise defined, all technical and scientific terms used herein have the same meaning as commonly understood by one of ordinary skill in the art. Standard techniques are used for molecular and biochemical methods and chemical methods.

It is to be noted that the term "a" or "an" entity refers to one or more of that entity; for example, "an anti-Aβ antibody," is understood to represent one or more antibodies which specifically bind to Aβ. As such, the terms "a" (or "an"), "one or more," and "at least one" can be used interchangeably herein.

Throughout the specification the word "comprise" or variations thereof such as "comprises" or "comprising" will be understood to include a stated element, integer or step, or group of elements, integers or steps, but not to exclude any other element, integer or steps, or groups of elements, integers or steps. The verb "comprising" includes the verbs "essentially consisting of" and "consisting of".

Unless stated otherwise, the terms "Aβ," "Abeta" and "beta-amyloid" are used interchangeably herein.

As used herein, the term "Aβ oligomers" refers to multimeric species of Aβ monomer that result from association of monomeric species. Aβ oligomers may include a dynamic range of dimers, trimers, tetramers and higher-order species following aggregation of synthetic Aβ monomers in vitro or following isolation/extraction of Aβ species from human brain or body fluids. Such Aβ oligomers are generally neurotoxic, soluble, globular, and non-fibrillar.

The term "Aβ fibrils" as used herein refers to insoluble species of Aβ that may be detected in human brain tissue. Amyloid fibrils are relatively stable and resistant to degradation. These species are believed to be immediate precursors to the extracellular amyloid plaque structures found in AD brain.

The term "Aβ monomer" as used herein refers to the direct product of the enzymatic cleavage by β-secretase and γ-secretase on the amyloid protein precursor (APP) in a cell-free or cellular environment. Cleavage of APP by β-secretase generates the Aβ species beginning at Asp 1 (numbering as to Aβ peptide sequence after cleavage), while γ-secretase liberate the C-terminus of Aβ, predominantly either at residues 40 or 42.

The term "affinity" as used herein refers to the strength of binding of a single molecule to its ligand and is typically expressed as the equilibrium dissociation constant ($K_D$) for the reversible binding of two agents. It is determined by the ratio of $k_{off}/k_{on}$ between the binding molecule taught herein and Aβ oligomers, Aβ fibrils, or Aβ monomers, respectively, $k_{off}$ and $k_{on}$ respectively denoting the rate of complex dissociation or association. $K_D$ and affinity are inversely related. The $K_D$ value relates to the concentration of binding molecule as taught herein and the lower the $K_D$ value, the higher is the affinity of the binding molecule.

As used herein, the term "binds" when referring to the interaction between the binding molecule taught herein and Aβ oligomers, Aβ fibrils, or Aβ monomers, respectively, means that the interaction is dependent upon the presence of a particular structure (e.g., an antigenic determinant or epitope) on the respective target.

As used herein, the term "specifically binds" or "binds specifically" is a term well understood in the art and shall be taken to mean that a binding molecule as taught herein reacts or associates more frequently, more rapidly, with greater duration and/or with greater affinity with Aβ oligomers than it does with alternative target, including Aβ fibrils and Aβ monomers. Methods to determine such specific (or preferential) binding are also well known in the art, for example as described in the Examples herein. More particularly, the binding molecule as taught herein binds with greater affinity to Aβ oligomers than it does to other targets, including Aβ fibrils and Aβ monomers. For example, an Aβ oligomer-specific binding molecule as taught herein specifically binds to Aβ oligomers with greater affinity (e.g. 2 fold, 10 fold, 20 fold or 40 fold or 60 fold or 80 fold to 100 fold or 150 fold or 200 fold greater affinity, more readily, and/or with greater duration than it binds to other antigens, including Aβ fibrils and Aβ monomers.

As used herein, the term "identity" means the percentage of identical nucleotide or amino acid residues at corresponding portions in two or more sequences when sequences are aligned to maximize sequence matching, i.e. taking into account gaps and insertions. Identity can be readily calculated using known methods, including, but not limited to these described in Computational Molecular Biology, Lesk A M ed. Oxford University Press New York, 1988; Computer Analysis of Sequence data, Part I Griffin A M and Griffin H G eds., Humana Press, New Jersey, 1994; Sequence analysis in molecular biology, von Heinje G, Academic Press, New Jersey, 1 994). Methods to determine identity are designed to give the largest match between the sequences tested. Moreover, methods to determined identity are codified in publicly available computer programs. Computer program methods to determine identity between two sequence include, but are not limited to, the GCG program package, BLASTP, BLASTN and FASTA. The well known Smith Waterman algorithm may also be used to determine identity. Sequence identity is preferably determined over the entire length of the sequence.

As used herein, the term "conservative amino acid substitution" refers to grouping of amino acids on the basis of certain common properties. A functional way to define common properties between individual amino acids is to analyze the normalized frequencies of amino acid changes between corresponding proteins of homologous organisms. According to such analysis, groups of amino acids may be defined where amino acids within a group exchange preferentially with each other, and therefore resemble each other most in their impact on the overall protein structure (Schulz G E and R H Schirmer, Principles of Protein Structure, Springer-Verlag). Examples of amino acid groups defined in this manner include:

(i) charged groups, consisting of Glu, Asp, Lys, Arg and His,
(ii) aromatic groups consisting of Phe, Tyr and Trp,
(iii) nitrogen ring group consisting of His and Trp,
(iv) slightly polar group consisting of Met and Cys etc.

As used herein, the term "promoter" includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

As used herein, the term "neurodegenerative disease" includes but is not limited to Alzheimer's Disease, mild cognitive impairment, fronto-temporal dementia, Lewy-body disease, Parkinson's disease, Pick's disease, Binswanger's disease; congophilic amyloid angiopathy, cerebral amyloid angiopathy, Down's syndrome, multi-infarct dementia, Huntington's Disease, Creutzfeldt-Jakob Disease, AIDS dementia complex, depression, anxiety disorder, phobia, Bell's Palsy, epilepsy, encephalitis, multiple sclerosis: neuromuscular disorders, neurooncological disorders, brain tumors, neurovascular disorders including stroke, neuroimmunological disorders, neurootological disease, neurotrauma including spinal cord injury, pain including neuropathic pain, pediatric neurological and neuropsychiatric disorders, sleep disorders, Tourette syndrome, mild cognitive impairment, vascular dementia, multi-infarct dementia, cystic fibrosis, Gaucher's disease other movement disorders and disease of the central nervous system (CNS) in general.

Unless stated otherwise, the terms "disorder," "disease" and "illness" are used interchangeably herein.

As used herein, the terms "treat" or "treatment" refer to both therapeutic treatment and prophylactic or preventative measures, wherein the object is to prevent or slow down (lessen) an undesired physiological change, infection, or disorder. Beneficial or desired clinical results include, but are not limited to, alleviation of symptoms, diminishment of extent of disease, stabilized (i.e., not worsening) state of disease, clearance or reduction of an infectious agent in a subject, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the infection, condition, or disorder as well as those prone to have the condition or disorder or those in which the condition or disorder is to be prevented.

The term "therapeutically effective amount" refers to an amount of therapeutic agent that, when administered alone or in combination with another therapeutic agent to a cell, tissue or subject, is effective to prevent or ameliorate the disease condition or the progression of the disease.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

The term "pharmaceutically acceptable" as used herein means acceptable for use in the pharmaceutical and veterinary arts, i.e. not being unacceptable from a toxological or other point of view. Pharmaceutically acceptable carriers include those conventionally used with peptide-based drugs, such as diluents, excipients, and the like. Guidance on drug formulations in general can be found, for example, in Remington's: The Science and Practice of Pharmacy, 21$^{st}$ ed., Lippincott Williams & Wilkins, 2005.

The term "i-bodies" as used herein refers to molecules that are designed so that they mimic the shape of the antigen binding domain of shark antibodies and their key stability features; these characteristics are engineered into a human protein. As unique compounds, i-bodies have a shark-like long binding loop that is absent in human antibodies and other next generation antibodies. This long binding loop and the human protein i-body scaffold form the i-body. The observation by Streltsov and colleagues (Protein Sci. 2005 November; 14(11): 2901-2909) that the VNAR was structurally similar to the I-set family of immunoglobulin domains (Igs) suggested that these are suitable scaffolds to engineer into a human equivalent of the VNAR. To this end, a human "i-body" scaffold from human neural cell adhesion molecule 1 (NCAM) was engineered by incorporating two binding regions (CDR1 and CDR3) into this protein, thus combining complementarity determining-like binding regions (CDRs) with the innate stability properties of a human Ig domain (WO 2016/109872, herein incorporated by reference).

DETAILED DESCRIPTION OF THE INVENTION

IgNARs/vNARs—General

Cartilaginous fish (sharks, rays, skates and chimaeras) express three different isotypes of antibodies, IgM, IgNARs (Immunoglobulin New Antigen Receptors) and the primordial IgW (Rumfelt L L. et al. BMC immunology 2004; 5:8; Rumfelt L L et al. Journal of immunology 2004; 173:1 129-39). IgNAR was first identified in the serum of the nurse shark (Ginglymostoma cirratum) (Greenberg A S et al. Nature 1995; 374:168-73). IgNAR is a homodimer of heavy chains devoid of light chains. Each chain of the secretory form consists of one variable domain followed by five constant domains, the last four being homologous to IgW constant domains. The antigen binding site is formed by only one single domain, referred to as 'vNAR' (variable domain of the New Antigen Receptor). Serum IgNAR levels range from approximately 0.1 mg/ml to 1 mg/ml.

All IgNARs identified to date are reported as having minimally variable loop regions analogous to conventional CDR1 and CDR2 loops, with diversity being concentrated in an elongated loop region analogous to a conventional CDR3 loop (Greenberg et al. Eur J Immunol. 1996 May; 26(5): 1123-9; Nuttall et al. 2001. Mol Immunol. August; 38(4): 313-26).

Despite having a reduced number of possible antigen binding loops (four across a single chain) compared to classical antibodies (six loops across two chains), vNAR domains bind antigens with surprisingly high affinities. Even from primary repertoires, where antigen binding is solely mediated by CDR3, vNAR molecules can be raised against a given antigen with affinities in the low nanomolar range: The highest recorded affinities for vNAR domains however, have been observed after immunization with an anti-albumin binding domain known as E06 achieving picomolar levels of affinity (Muller et al., MAbs 2012; 4:673-85).

The tremendous diversity found at the sequence-level of the CDR3-loop of IgNAR, as well as the multiplicity of the structural topologies formed by the antigen-binding site of the vNAR domain, render IgNARs or other antigen-binding molecules comprising the antigen-binding portion of the IgNAR, the vNAR, promising alternatives to conventional antibodies.

vNARs or vNAR based antigen-binding molecules have several advantages over IgGs.

vNARs have a long antigen binding region (10-20 amino acids vs 10-12 in a normal IgG). This means that the contact surface of the antibody with the antigen is significantly larger in vNAR. Furthermore the antigen binding domain protrudes into the solution whereas the antigen binding domains of typical IgG and other antibody analogues are more shallow. These elements translate into high affinity with respect to reference IgGs, especially for antigen proteins with crevices/clefts.

vNARs are extremely stable. Sharks have a lot of salt and ureum in their plasma, which are both protein denaturants, which forced nature to come up with proteins that are stable in such an harsh environment.

vNARs are small in comparison to IgGs (15 kDa for vNARs vs. 150 kDa for IgGs). The small size of vNARS leads to enhanced tissue penetration, as well as high renal clearance, which may be particularly advantageous for imaging applications.

vNARs can be produced in bacteria, which makes protein engineering easy and large-scale production possible.

vNARs can easily be modified site-specifically to specifically attach a broad range of moieties including biotin, fluorescent labels, PET tracer labels etc., thereby allowing many applications including PET imaging.

Aβ Oligomer-Specific Binding Molecules

The present disclosure provides an amyloid beta peptide (Aβ)-oligomer-specific antigen binding molecule displaying the following characteristics:

an affinity for Aβ-oligomers of less than 1 nM; and
an at least 50-fold greater specificity for Aβ-oligomers than for Aβ-fibrils.

The affinity is preferably determined using an ELISA. Preferably, Aβ oligomers, e.g. as prepared essentially as described by Dahlgren et al., (2002. J Biol Chem. 2002 Aug. 30; 277(35):32046-53) or preferably as provided with the Perkin Elmer Amyloid Oligomers AlphaLISA High-Specificity Detection Kit (AL334F), or Aβ fibrils, e.g. as prepared essentially as described by Dahlgren et al., (2002. J Biol Chem. 2002 Aug. 30; 277(35):32046-53), are immobilized on a solid support and then incubated with various concentrations antigen binding molecule as taught herein. Antigen binding molecule bound to Aβ oligomers or Aβ fibrils may subsequently be detected using a suitable detection agent specifically binding to the antigen binding molecule.

Alternatively, Aβ oligomers, e.g. as prepared essentially as described by Dahlgren et al., (2002. J Biol Chem. 2002 Aug. 30; 277(35):32046-53) or preferably as provided with the Perkin Elmer Amyloid Oligomers AlphaLISA High-Specificity Detection Kit (AL334F), or Aβ fibrils, e.g. as prepared essentially as described by Dahlgren et al., (2002. J Biol Chem. 2002 Aug. 30; 277(35):32046-53), may be immobilized to a solid support suitable for Surface Plasmon resonance measurements in which the binding of the antibody can be followed in real-time.

Preferably, the coating density of the oligomer should be kept as low as possible so as to minimize the chance that the antigen binding molecule binds to two immobilized oligomers at the same time, which would lead to a high apparent affinity that is not related to the true thermodynamic binding affinity in solution.

The present disclosure also provides an amyloid beta peptide (Aβ)-oligomer-specific antigen binding molecule comprising an amino acid sequence comprising the structure X-CDR1-Y-CDR3-Z; in which: CDR1 comprises the amino acid sequence of amino acid residues 27-32 of SEQ ID NO:1 (QNGWSR) or an amino acid sequence having at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to the amino acid sequence of amino acid residues 27-32 of SEQ ID NO:1; and CDR3 comprises the amino acid sequence of amino acid residues 85-102 of SEQ ID NO:1 (LLNPRREEFWFSRRYPVV) or an amino acid sequence having at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to the amino acid sequence of amino acid residues 85-102 of SEQ ID NO:1.

The Aβ-oligomer-specific antigen binding molecules taught herein can be used to modulate, and in particularly inhibit or prevent Aβ-oligomer mediated pathways resulting in Aβ fibril, and thereby Aβ-plaque, formation. As such, the Aβ-oligomer-specific antigen binding molecule taught herein can be used for the prevention and treatment of Aβ-oligomer-related or Aβ-oligomer-mediated diseases and disorders, as well as for the diagnosis, progression, and/or prognosis of Aβ-oligomer-related or Aβ-oligomer-mediated diseases and disorders.

The Aβ-oligomer-specific antigen binding molecules taught herein can also be used to modulate, and in particularly inhibit or prevent Aβ-oligomer mediated pathways, including pathways that are mediated by a direct interaction of Aβ-oligomer with cellular binding moieties such as receptors, or those that result in Aβ fibril, and thereby Aβ-plaque, formation.

The Aβ-oligomer-specific antigen binding molecules taught herein provide advantages over other Aβ-specific antigen binding molecules. They are capable of binding their target with high affinity and high specificity. Particularly, the Aβ-oligomer-specific antigen binding molecules taught herein are specific for Aβ-oligomers rather than Aβ monomers or Aβ fibrils. In an embodiment, the Aβ-oligomer-specific antigen binding molecules taught herein bind at least 10-, 20-, 30-, 40-, or 50-fold stronger to Aβ-oligomer as compared to Aβ monomers as may be determined using an ELISA assay. In an embodiment, the Aβ-oligomer-specific antigen binding molecules taught herein bind at least 10-, 25-, 50-, 100-, or 200-fold stronger to Aβ-oligomer as compared to Aβ fibrils as may be determined using an ELISA assay./pct In an embodiment, the Aβ-oligomer-specific antigen binding molecules taught herein bind to Aβ-oligomers with an affinity of less than 10 µM, less than 5 µM, less than 1 µM, less than 750 nM, less than 500 nM, less than 250 nM, less than 100 nM, less than 75 nM, less than 50 nM, less than 25 nM, less than 20 nM, less than 15 nM, less than 10 nM, less than 5 nM, or less than 1 nM.

Whilst in IgGs, such high oligomer specificity relative to monomer binding could have been achieved through binding avidity (for example, both arms of an IgG may simultaneously bind to repeating epitopes on the same Aβ derived aggregate molecule, whereas monomeric Aβ can only bind to one arm on the IgG), this is not the case for the binding molecule of the present invention. For this reason, the bivalent aggregate binding observed in IgGs can be 100 to 1000 fold stronger for aggregates relative to monomers. Since some epitopes (most notably the N-terminus) are available on both oligomers and fibrils, such antibodies recognize both antigens with similar affinities.

Since the binding molecule of the present invention is monomeric, binding avidity can not explain oligomer specificity. From the observation that both Aβ monomers and Aβ fibrils are detected only at very low level, it can be concluded that the Aβ-oligomer-specific antigen binding molecules taught herein bind a conformational epitope on Aβ-oligomers.

Additionally, the Aβ-oligomer-specific antigen binding molecules taught herein are small in size and are highly stable, which may lead to alternative routes of administration and lower dose form, less frequent dosage, and less side effects than known Aβ-specific antigen binding molecules currently proposed for use in the prevention or treatment of amyloid beta peptide (Aβ)-related diseases or disorders.

Moreover, the relatively small size allows tailoring of half-life which is advantageous, particularly when the molecules of the present invention are used as an imaging agent or in the delivery of a required dose for a set period of time.

The % identity of a polypeptide or polynucleotide may be determined by GAP (Needleman and Wunsch, 1970) analysis (GCG program) with a gap creation penalty=5, and a gap extension penalty=0.3.

For purposes of the present disclosure, alignments of sequences and calculation of homology scores are done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 1 83:63-98).

The present disclosure contemplates variant forms of binding protein of the disclosure. For example, such a variant binding protein comprises one or more conservative amino acid substitutions compared to a sequence set forth herein. In some examples, the binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), /3-branched side chains (e.g., threonine, valine, isoleucine) and aromatic side chains (e.g., tyrosine, phenylalanine, tryptophan, histidine). Hydropathic indices are described, for example in Kyte and Doolittle (1982) and hydrophylic indices are described in, e.g., U.S. Pat. No. 4,554,101, which is herein incorporated by reference.

The present disclosure also contemplates non-conservative amino acid changes. For example, of particular interest are substitutions of charged amino acids with another charged amino acid and with neutral or positively charged amino acids. In some examples, the binding protein comprises 10 or fewer, e.g., 9 or 8 or 7 or 6 or 5 or 4 or 3 or 2 or 1 non-conservative amino acid substitutions.

The present disclosure also provides an amyloid beta peptide (Aβ)-oligomer-specific antigen binding molecule, preferably comprising an amino acid sequence comprising the structure X-CDR1-Y-CDR3-Z; in which: CDR1 comprises the amino acid sequence of amino acid residues 27-32 of SEQ ID NO:1 (QNGWSR) and CDR3 comprises the amino acid sequence of amino acid residues 85-102 of SEQ ID NO:1 (LLNPRREEFWFSRRYPVV) and wherein at most 1, 2 or 3 amino acids in CDR1 are substituted, preferably wherein the substitution is a conservative amino acid substitution, and/or wherein at most 1, 2 or 3 amino acids in CDR3 are substituted, preferably wherein the substitution is a conservative amino acid substitution. Preferably the amyloid beta peptide (Aβ)-oligomer-specific antigen binding molecule has an affinity for Aβ-oligomers of less than 1 nM and an at least 50-fold greater specificity for Aβ-oligomers than for Aβ-fibrils. In a preferred embodiment only CDR1 comprises 1, 2 or 3 amino acid substitutions. In a preferred embodiment only CDR3 comprises 1, 2 or 3 amino acid substitutions. Preferably only 1 amino acid is substituted in CDR1, in CDR 3 or in both CDR1 and CDR3.

In an embodiment, the Aβ-oligomer-specific antigen binding molecule taught herein is preceded by a signal peptide (sometimes referred to as signal sequence, targeting signal, localization signal, localization sequence, transit peptide, leader sequence or leader peptide) to achieve e.g. secretion of the binding molecule. In an embodiment, the signal peptide may comprise or consist of the amino acid sequence shown in SEQ ID NO:3.

In a suitable embodiment, X represents Framework Region (FW)1, Y represents FW2-Hypervariable Region 2 (HV2)-FW3a-HV4-FW3a, and Z represents FW4 as present in vNARs.

In an embodiment, X comprises an amino acid sequence having at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to the amino acid sequence of amino acid residues 1-26 of SEQ ID NO:1; Y comprises an amino acid sequence having at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to the amino acid sequence of amino acid residues 33-84 of SEQ ID NO:1; and/or Z comprises an amino acid sequence having at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to the amino acid sequence of amino acid residues 103-114 of SEQ ID NO:1.

In an embodiment, the Aβ-oligomer-specific antigen binding molecule taught herein comprises the amino acid sequence of SEQ ID NO:1, or an amino acid sequence having at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to the amino acid sequence of SEQ ID NO:1.

In an embodiment, the antigen binding molecule taught herein comprises a scaffold region and CDR1 and/or CDR3 regions as taught herein (for a suitable scaffold region, see WO2016/109872, herein incorporated by reference). In one suitable example, the scaffold region is based upon Domain 1 of human NCAM1 (Neural Cell Adhesion Molecule 1) as shown in SEQ ID NO:2. For example, the scaffold region may comprise an amino acid sequence which has at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to amino acids 1-26, 33-79, and 88-97 of the amino acid sequence of SEQ ID NO:2, wherein the amino acid residues 27-32 and 80-87 of SEQ ID NO:2 are replaced by the CDR1 and CDR3 amino acid residues, respectively, as taught herein above.

Thus, in an embodiment, X comprises an amino acid sequence that has at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to amino acids 1-26 of the amino acid sequence of SEQ ID NO:2; and/or Y comprises an amino acid sequence which has at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to amino acids 33-79 of the amino acid sequence of SEQ ID NO:2; and/or Z comprises an amino acid sequence which has at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to amino acids 88-97 of the amino acid sequence of SEQ ID NO:2.

In another embodiment, the antigen binding molecule taught herein comprises an i-body scaffold region and CDR1 and/or CDR3 regions as taught herein (for a suitable i-body scaffold region, see WO2016/109872, herein incorporated by reference). In one suitable example, the scaffold region is the one shown in SEQ ID NO:4. For example, the i-body scaffold region may comprise an amino acid sequence which has at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to amino acids 1-26, 33-79, and 81-90 of the amino acid sequence of SEQ ID NO:4, wherein the amino acid residues 27-32 and 80 of SEQ ID NO:4 are replaced by the CDR1 and CDR3 amino acid residues, respectively, as taught herein above.

Thus, in an embodiment, X comprises an amino acid sequence that has at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to amino acids 1-26 of the amino acid sequence of SEQ ID NO:4; and/or Y comprises an amino acid sequence which has at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to amino acids 33-79 of the amino acid sequence of SEQ ID NO:4; and/or Z comprises an amino acid sequence which has at least 50%, such as at least 55%, at least 60%, at least 65%, at least 70%, at least 75%, at least 80%, at least 85%, at least 90%, or at least 95%, 96%, 97%, 98%, 99%, or 100%, sequence identity to amino acids 81-90 of the amino acid sequence of SEQ ID NO:4.

Nucleic Acid Molecules, Vectors, and Host Cells

The disclosure also provides for a nucleic acid molecule encoding the Aβ-oligomer-specific antigen binding molecule as taught herein, an expression vector comprising such nucleic acid molecule, and a host cell comprising such nucleic acid molecule or expression vector. The disclosure also provides for the use of such nucleic acid molecule or expression vector as, for example, a medicament or in the treatment or prevention of a disease, preferably a neurodegenerative disease.

In one example, a polypeptide of the disclosure is produced by culturing a cell line, e.g., an E. coli cell line under conditions sufficient to produce the protein, e.g., as described herein and/or as is known in the art.

In the case of a recombinant Aβ-oligomer-specific antigen binding molecule as taught herein, nucleic acid encoding such molecule is placed into one or more expression constructs, e.g., expression vector(s), which is/are then transfected into host cells, e.g., bacterial cells such as E. coli cells, yeast cells, insect cells, or mammalian cells. Exemplary mammalian cells include simian COS cells, or Chinese Hamster Ovary (CHO) cells. Exemplary bacterial cells include BL21(DE3), BL21(DE3)-pLysS, and the like.

Molecular cloning techniques are known in the art and described, for example in Ausubel F M (1987) Current Protocols in Molecular Biology. New York, N.Y., John Wiley & Sons or Sambrook, Fritsch and Maniatis Molecular Cloning: a laboratory manual Cold Spring Harbor N.Y. Cold Spring Harbor Laboratory Press. A wide variety of cloning and in vitro amplification methods are suitable for the construction of recombinant nucleic acids.

Many vectors for expression in cells are available. The vector components generally include, but are not limited to, one or more of the following: a signal sequence, a sequence encoding a polypeptide of the present disclosure (e.g., derived from the information provided herein), an enhancer element, a promoter, and a transcription termination sequence. The skilled artisan will be aware of suitable sequences for expression of a protein. Many known techniques and protocols for manipulation of nucleic acid, for example, in the preparation of nucleic acid constructs, mutagenesis, introduction of DNA into cells and gene expression and analysis of protein are described in for example, Ausubel F M (1987) Current Protocols in Molecular Biology. New York, N.Y., John Wiley & Sons. A wide variety of host/expression vector combinations can be employed in expressing the Aβ-oligomer-specific antigen binding molecule of the disclosure.

Means for introducing the isolated nucleic acid molecule or a gene construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine and/or cellfectin, PEG-mediated DNA uptake, electroporation, viral transduction and microparticle bombardment such as by using DNA-coated tungsten or gold particles, and the like.

Also provided herein is a recombinant host cell which comprises one or more polynucleotide constructs. A polynucleotide encoding an Aβ-oligomer-specific antigen binding molecule of the present disclosure is encompassed herein as are methods of production of Aβ-oligomer-specific antigen binding molecule which method comprises expression from a polynucleotide. Expression can be achieved, for example, by culturing under appropriate conditions recombinant host cells containing the polynucleotide.

The host cells used to produce the binding molecule of this disclosure may be cultured in a variety of media, depending on the cell type used. One skilled in the art will be able to select the proper vectors, expression control sequences, and hosts without undue experimentation to accomplish the desired expression.

A polynucleotide encoding an Aβ-oligomer-specific antigen binding molecule of the present disclosure can be prepared recombinantly/synthetically, in addition to, or rather than cloning. The polynucleotide can be designed with the appropriate codons for the Aβ-oligomer-specific antigen binding molecule. In general, one will select preferred codons for an intended host if the sequence will be used for expression. The complete polynucleotide can be assembled from overlapping oligonucleotides prepared by standard methods and assembled into a complete coding sequence.

In a preferred embodiment, the expression vector is a Adeno-Associated Virus (AAV) viral vector (including recombinant AAV viral vectors) comprising the nucleic acid molecule as taught herein. Such AAV viral vectors are well-known to the skilled person, as well as its use in gene therapy (see, for example, Naso et al. (2017) BioDrugs. doi: 10.1007/s40259-017-0234-5 for details on Adeno-Associated Virus (AAV) Vector Designs and use in clinical settings). Other examples are provides in for example, EP 1257656, EP 0954592, EP 0488528, EP1082444 and many others.

Adeno-associated virus (AAV) vectors are considered useful for gene therapy, including CNS gene therapy because they have a favourable toxicity and immunogenicity profile, are able to transduce CNS cells, and are able to mediate long-term expression in the CNS (Kaplitt et al. (1994) Nat. Genet. 8:148-154; Bartlett et al. (1998) Hum. Gene Ther. 9:1181-1186; and Passini et al. (2002) J. Neurosci. 22:6437-6446). Cells transduced by AAV vectors may express the therapeutic transgene product (here the Aβ-oligomer-specific antigen binding molecule), to mediate beneficial effects intracellularly. These cells may also secrete the therapeutic transgene product (if needed by including a suitable leader signal sequence) to exert an extracellular effect, such as binding to Aβ-oligomers. The extracellular transgene product may also be subsequently taken up by distal cells where it may mediate its beneficial effects. This latter process has been described as cross-correction (Neufeld et al. (1970) Science 169:141-146).

In one aspect, the invention also provides a method to deliver the nucleic acid molecule encoding the Aβ-oligomer-specific antigen binding molecule as taught herein to the CNS, or brain of a subject by administration of an AAV viral vector (including recombinant AAV viral vectors) comprising the nucleic acid molecule encoding the Aβ-oligomer-specific antigen binding molecule as taught herein. The AAV viral vector as taught herein may, for example be used in the prevention or treatment of a condition as taught herein, or as a medicament, or pharmaceutical composition.

The skilled person is well-aware how to prepare, design and use such AAV viral vectors, including those as taught herein. AAV vectors are derived from single-stranded (ss) DNA parvoviruses that are nonpathogenic for mammals (reviewed in Muzyscka (1992) Curr. Top. Microb. Immunol., 158:97-129). Briefly, recombinant AAV-based vectors have the rep and cap viral genes that account for 96% of the viral genome removed, leaving the two flanking 145-base-pair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may be maintained episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In the invention, AAV of any serotype can be used. The serotype of the AAV viral vector used in certain embodiments of the invention is selected from the group consisting from AAV1, AAV2, AAV3, AAV4, AAV5, AAV6, AAV7, and AAV8 (see, e.g., Gao et al. (2002) PNAS, 99:11854-11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome (Auricchio et al., (2001) Hum. Mol. Genet., 10 (26):3075-81). Preferably the AAV is AAV5.

Methods for measuring binding specificity of an anti-Aβ antibody or antigen-binding fragment, variant, or derivative thereof, include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., Immunity 13:633-642 (2000); Kumanogoh et al., J Immunol 169:1175-1181 (2002); Watanabe et al., J Immunol 167: 4321-4328 (2001); Wang et al., Blood 97:3498-3504 (2001); and Giraudon et al., J Immunol 172(2):1246-1255 (2004), all of which are herein incorporated by reference.

Conjugate and Multimer of the Aβ-Oligomer-Specific Antigen Binding Molecule

The present disclosure also provides a conjugate (e.g., an immunoconjugate) comprising an Aβ-oligomer-specific antigen binding molecule described herein and one or more agents.

The agent may be, for example, a therapeutic agent, a toxin, a detectable label or an agent which extends the half-life of the Aβ-oligomer-specific antigen binding molecule, or any combination thereof. In one example, the agent is polyethylene glycol (PEG). In one example the agent which extends the half-life of the Aβ-oligomer-specific antigen binding molecule binds to a serum protein (e.g. albumin) or an Fc portion of an immunoglobulin. Alternatively or in addition the agent may provide the construct with certain effector functions such as agents that direct the oligomer bound complex to specific cell types such as macrophages.

In another example the Aβ-oligomer-specific antigen binding molecule taught herein may be linked to a label such as a radioisotope to provide a conjugate.

Said conjugate can be prepared using methods well-known in the art.

The present disclosure also provides a multimer comprising two or more Aβ-oligomer-specific antigen binding molecules as described herein. The Aβ-oligomer-specific antigen binding molecules may comprise the same or different amino acid sequences. For example, in its simplest form, at least two Aβ-oligomer-specific antigen binding molecules are directly linked via a suitable linker or sequence or spacer. For example, the linker or spacer can be between 1 and 50 amino acids.

The present disclosure also provides for multivalent or multispecific molecules comprising the Aβ-oligomer-specific antigen binding molecule taught herein (including bi-specific antigen binding molecules). In one example the disclosure provides an Aβ-oligomer-specific antigen binding molecule of the present disclosure linked to a polypeptide directed to a target other than Aβ-oligomers, including but not limited to, human serum albumin to increase half-life.

Pharmaceutical Composition Comprising the Aβ-Oligomer-Specific Antigen Binding Molecule or an Expression Vector Comprising a Nucleic Acid Molecule Encoding Such the Aβ-Oligomer-Specific Antigen Binding Molecule, Preferably Wherein the Expression Vector is a AAV Viral Vector Comprising a Nucleic Acid Molecule Encoding Such the Aβ-Oligomer-Specific Antigen Binding Molecule.

In an aspect, the present invention pertains to a pharmaceutical composition comprising the Aβ-oligomer-specific antigen binding molecule, conjugate, multimer or expression vector, preferably wherein the expression vector is an AAV viral vector, as taught herein and a pharmaceutically acceptable carrier.

The pharmaceutically acceptable carrier may comprise a diluent, excipient, and the like. The selection of carrier depends on the intended mode of administration of the composition. The Aβ-oligomer-specific antigen binding molecule, conjugate or multimer as taught herein may be formulated for parenteral, topical, oral, or local administration, aerosol administration, or transdermal administration, for prophylactic or therapeutic treatment. The pharmaceutical compositions can be administered in a variety of unit dosage forms depending upon the method of administration.

The Aβ-oligomer-specific antigen binding molecule, conjugate, multimer or expression vector, preferably wherein the expression vector is an AAV viral vector, taught herein may be formulated for administration by infusion, or by injection, for example subcutaneously, intramuscularly, intrathecal, intracranial, intracerebroventricular, direct tissue or organ injection or intravenously, and may therefore be formulated as aqueous solutions in sterile form, optionally buffered and/or made isotonic. The Aβ-oligomer-specific antigen binding molecule, conjugate multimer or expression vector, preferably wherein the expression vector is an AAV viral vector, taught herein may, for example, be administered in distilled water, or in saline, phosphate buffered saline, or 5% dextrose solution.

Compositions for oral administration via tablet, capsule, or suspension may be prepared using adjuvants, including, without limitation, sugars, such as lactose, glucose or sucrose; starches such as corn starch or potato starch; cellulose or derivatives thereof, including sodium carboxymethylcellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil, or corn oil; polyols such as propylene glycol, glycerine, sorbital, mannitol, or polyethylene glycol; agar; alginic acids; water; isotonic saline; or phosphate buffered solutions. Wetting agents, lubricants, stabilizers, tableting agents, antioxidants, preservatives, coloring agents and flavoring agents may further be present.

Aerosol formulations, e.g., for nasal delivery, may also be prepared, e.g., with suitable propellant adjuvants.

Other adjuvants may also be added to the composition regardless of the administration form, for example, antimicrobial agents may be added to the composition to prevent microbial growth over prolonged storage periods.

Pharmaceutical compositions are typically sterile and stable under conditions of manufacture and storage.

Upon formulation, Aβ-oligomer-specific antigen binding molecule, conjugate multimer or expression vector, preferably wherein the expression vector is an AAV viral vector, as taught herein will be administered in a manner compatible with the dosage formulation and in such an amount as is therapeutically/prophylactically effective. Suitable dosages of Aβ-oligomer-specific antigen binding molecule, conjugate multimer or expression vector, preferably wherein the expression vector is an AAV viral vector, will vary depending on the specific molecule, conjugate or multimer, the mode of administration, the condition to be treated, and/or the subject being treated. The skilled person is capable of determining a suitable dosage, e.g., by commencing with a sub-optimal dosage and incrementally modifying the dosage to determine an optimal or useful dosage.

For administration of the Aβ-oligomer-specific antigen binding molecule, conjugate or multimer as taught herein, the dosage may range from about 0.00001 to about 100 mg/kg, about 0.0001 to about 10 mg/kg, or about 0.001 to about 1 mg/kg, of the subject's body weight.

The composition may be administered once per day, once per week, once every two weeks, once a month, once every three months, or the like.

Pharmaceutical compositions of the present disclosure may be administered in combination with other agents, i.e. as a combination therapy. When administered in combination with another agent, the Aβ-oligomer-specific antigen binding molecule, conjugate multimer or expression vector, preferably wherein the expression vector is an AAV viral vector, taught herein may be administered in either order sequentially or simultaneously.

The amount of Aβ-oligomer-specific antigen binding molecule, conjugate multimer or expression vector, preferably wherein the expression vector is an AAV viral vector, which may be combined with a pharmaceutically acceptable carrier to produce a single dosage form will generally be that amount of the Aβ-oligomer-specific antigen binding molecule, conjugate multimer or expression vector, preferably wherein the expression vector is an AAV viral vector, that produces a prophylactic or therapeutic effect.

Dosage regimens are adjusted to provide the optimal prophylactic or therapeutic response. For example, a single bolus may be administered, or several divided doses may be administered in time.

Methods/Uses of the Aβ-Oligomer-Specific Antigen Binding Molecule, Conjugate Multimer or expression vector, preferably wherein the expression vector is an AAV viral vector.

The Aβ-oligomer-specific antigen binding molecule, conjugate, multimer or expression vector, preferably wherein the expression vector is an AAV viral vector, as taught herein has numerous in vitro and in vivo diagnostic and therapeutic uses. For example, the molecule, conjugate, multimer or expression vector, preferably wherein the expression vector is an AAV viral vector, can be administered to human subjects, e.g., in vivo, or to cells in culture, in vitro, to treat, prevent or to diagnose a variety of disorders characterized by the involvement of β-amyloid oligomers.

In an aspect, the Aβ-oligomer-specific antigen binding molecule, conjugate, multimer or expression vector, preferably wherein the expression vector is an AAV viral vector, as taught herein can be used as a medicament, whereas in another aspect, the Aβ-oligomer-specific antigen binding molecule, conjugate, multimer or expression vector, preferably wherein the expression vector is an AAV viral vector, as taught herein may be used as a diagnostic agent.

The invention also provides an Aβ-oligomer-specific antigen binding molecule, conjugate, multimer or expression vector, preferably wherein the expression vector is an AAV viral vector, as taught herein for treating β-amyloid related diseases or conditions, such as for use in the treatment or prevention of neurodegenerative diseases, including, but not limited to, Alzheimer's Disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, dementia, pre-dementia, Cognitive Dysfunction Syndrome, loss of cognition, and Gaucher's disease.

In another aspect, the present disclosure provides a method of reducing Aβ-oligomer levels a subject, e.g., in cerebrospinal fluid or brain plasma or blood plasma of a subject, said method comprising the step of administering to said subject an Aβ-oligomer-specific antigen binding molecule, conjugate, multimer or expression vector, preferably wherein the expression vector is an AAV viral vector, as taught herein.

Diagnostic Methods

As will be apparent to the skilled person, the present disclosure also contemplates imaging methods using an Aβ-oligomer-specific binding molecule taught herein. For imaging, a Aβ-oligomer-specific binding molecule is generally conjugated to a detectable label, which can be any molecule or agent that can emit a signal that is detectable by imaging. However, a secondary labelled compound that specifically binds to an Aβ-oligomer-specific binding molecule as taught herein may also be used. Exemplary detectable labels include a protein, a radioisotope, a fluorophore, a visible light emitting fluorophore, infrared light emitting fluorophore, a metal, a ferromagnetic substance, an electromagnetic emitting substance a substance with a specific magnetic resonance (MR) spectroscopic signature, an X-ray absorbing or reflecting substance, or a sound altering substance.

The Aβ-oligomer-specific binding molecule as taught herein (and, if used, the labelled secondary compound) can be administered either systemically or locally to an organ, or tissue to be imaged, prior to the imaging procedure. Administration may be directly or by administration of an expression vector, preferably wherein the expression vector is an AAV viral vector, as taught herein. Generally, the Aβ-oligomer-specific binding molecule is administered in doses effective to achieve the desired image of a tissue or organ. Such doses may vary widely, depending upon the particular Aβ-oligomer-specific binding molecule employed, condition to be imaged, tissue or organ subjected to the imaging procedure, the imaging equipment being used, and the like.

In an embodiment, the Aβ-oligomer-specific binding molecule is used as in vivo optical imaging agents of tissues and organs in various biomedical applications including, but not limited to, imaging of brains, tomographic imaging of organs, monitoring of organ functions, coronary angiography, fluorescence endoscopy, laser guided surgery, photoacoustic and sonofluorescence methods, and the like.

Examples of imaging methods include magnetic resonance imaging (MRI), MR spectroscopy, radiography, computerized tomography (CT), ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

For example, PET imaging of amyloid plaque is one of the ways to detect AD (along with amyloid beta in CSF). An Aβ-oligomer-specific PET might be of (clinical) diagnostic utility, as Aβ-oligomer rather than whole amyloid in the brain could be detected using Immuno-PET.

In an embodiment, an imaging agent is tested using an in vitro or in vivo assay prior to use in humans.

In yet another aspect, the present disclosure teaches a method of measuring Aβ-oligomer levels in a test sample, said method comprising the steps of:
(a) contacting a test sample with an Aβ-oligomer-specific antigen binding molecule, conjugate, or multimer as taught herein under conditions sufficient to form a binding molecule or conjugate or multimer/Aβ-oligomer complex; and
(b) detecting the binding molecule or conjugate or multimer/Aβ-oligomer complex.

The skilled person readily knows that detection of the binding molecule or conjugate or multimer/Aβ-oligomer complex may also occur through the Aβ-oligomer released from the complex or through the binding molecule or conjugate or multimer released from the complex, as may be done using mass spectrometry.

To the extent that a method of the present disclosure is performed in vitro, on an isolated tissue sample, rather than as an in vivo based screen, reference to "sample" should be understood as a reference to any sample of biological material derived from a subject such as, but not limited to, a body fluid (e.g., cerebrospinal fluid, or brain plasma, or blood plasma), cellular material, tissue biopsy specimens, for example a brain biopsy specimen, or surgical specimens.

The sample which is used according to a method of the present disclosure may be used directly or may require some form of treatment prior to use. For example, a biopsy or surgical sample may require homogenization or other form of cellular dispersion prior to use. Furthermore, to the extent that the biological sample is not in liquid form, (if such form is required or desirable) it may require the addition of a reagent, such as a buffer, to mobilize the sample.

As will be apparent from the preceding description, such an assay may require the use of a suitable control, e.g. a normal or healthy individual or a typical population, e.g., for quantification.

A "healthy subject" is one that has not been diagnosed as suffering from an Aβ-oligomer-related disease or disorder and/or is not at risk of developing such disease or disorder.

Alternatively, or in addition, a suitable control sample is a control data set comprising measurements of the marker being assayed for a typical population of subjects known not to suffer from a condition.

In one example, a reference sample is not included in an assay. Instead, a suitable reference sample is derived from an established data set previously generated from a typical population. Data derived from processing, analyzing and/or assaying a test sample is then compared to data obtained for the sample population.

Therefore, in an embodiment, the level of binding molecule or conjugate or multimer/Aβ-oligomer complex is determined. Said level of binding molecule or conjugate or multimer/Aβ-oligomer complex may be compared to the level of binding molecule or conjugate or multimer/Aβ-oligomer complex detected in a sample derived from a healthy subject, or to a reference value derived from a population, e.g. a population of healthy subjects.

Said method may be intended for diagnosing a subject suffering from a neurodegenerative disease, such as selected from the group consisting of Alzheimer's disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, and Gaucher's disease.

Various diagnostic assay techniques known in the art can be used, such as competitive binding assays, direct or indirect sandwich assays and immunoprecipitation assays conducted in either heterogeneous or homogeneous phases (Zola, Monoclonal Antibodies: A Manual of Techniques, CRC Press, Inc. (1987) pp. 147-158). The binding molecules used in the diagnostic assays can be labeled with a detectable moiety. The detectable moiety directly or indirectly produces a detectable signal. For example, the detectable moiety can be a radioisotope, such as $^3H$, $^{14}C$, $^{32}P$, $^{35}S$, or $^{125}I$, a fluorescent or chemiluminescent compound, such as fluorescein isothiocyanate (FITC), Texas red, cyanin, photocyan, rhodamine, or luciferin, or an enzyme, such as alkaline phosphatase, /3-galactosidase or horseradish peroxidase. Any method known in the art for conjugating the antibody to the detectable moiety can be employed, includ- The present invention further provides a method of assessing disease progression in a subject being treated for a neurodegenerative disease comprising the steps of:

(a) contacting a first test sample taken at a first time point with an Aβ-oligomer-specific antigen binding molecule, conjugate, or multimer as taught herein under conditions sufficient to form a binding molecule or conjugate or multimer/Aβ-oligomer complex and detecting the level of binding molecule or conjugate or multimer/Aβ-oligomer complex;

(b) contacting a second test sample taken at a second time point with an Aβ-oligomer-specific antigen binding molecule, conjugate, or multimer as taught herein under conditions sufficient to form a binding molecule or conjugate or multimer/Aβ-oligomer complex and detecting the level of binding molecule or conjugate or multimer/Aβ-oligomer complex; and (c) comparing the level of binding molecule or conjugate or multimer/Aβ-oligomer complex of the first test sample to the level of binding molecule or conjugate or multimer/Aβ-oligomer complex of the second test sample.

In an embodiment, an increased level of binding molecule or conjugate or multimer/Aβ-oligomer complex in the second test sample compared to that in the first test sample is indicative of progression of said neurodegenerative disease, preferably selected from the group consisting of Alzheimer's Disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, and Gaucher's disease, in the subject.

In an embodiment, a decreased level of binding molecule or conjugate or multimer/Aβ-oligomer complex in the second test sample compared to that in the first test sample is indicative of effectiveness of the treatment of said neurodegenerative disease, preferably selected from the group consisting of Alzheimer's Disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, and Gaucher's disease, in the subject.

Kits

In an aspect, the present disclosure provides a kit or pharmaceutical package suitable for detecting Aβ-oligomers, comprising the Aβ-oligomer-specific antigen binding molecule as taught herein, a conjugate as taught herein, a multimer as taught herein or expression vector, preferably wherein the expression vector is an AAV viral vector, as taught herein.

In an embodiment, said kit is intended for the administration of the Aβ-oligomer-specific antigen binding molecule as taught herein, a conjugate as taught herein, or a multimer as taught herein, or expression vector, preferably wherein the expression vector is an AAV viral vector, as taught herein.

Pharmaceutical packages and kits may further include an excipient, a carrier, a buffering agent, a preservative or a stabilizing agent in a pharmaceutical formulation. Each component of the kit can be enclosed within an individual container and all of the various containers can be within a single package. Kits as taught herein can be designed for room temperature or cold storage. Additionally, the preparations can contain stabilizers to increase shelf life of the kits and may include, for example, bovine serum albumin (BSA) or other known conventional stabilizers. Where the compositions comprising the Aβ-oligomer-specific antigen binding molecule as taught herein, the conjugate as taught herein, or the multimer as taught herein are lyophilized, the kit can contain further preparations of solutions to reconstitute the preparations. Acceptable solutions are well known in the art and include, for example, pharmaceutically acceptable phosphate buffered saline (PBS)

The pharmaceutical packages or kits provided herein can further include other moieties such as, for example, other agents that may be used to co-treat the neurodegenerative diseases taught herein.

Pharmaceutical packages and kits of the present invention may further include the components for an assay provided herein, such as, for example, an ELISA assay. Alternatively, preparations of the kits may be used in immunoassays, such as immunohistochemistry to test patient tissue biopsy sections.

Pharmaceutical packages and kits of the present invention can further include a label specifying, for example, a product description, mode of administration and indication of treatment. Pharmaceutical packages provided herein can include any of the compositions as described herein. The pharmaceutical package can further include a label for preventing, reducing the risk of, or treating any of the disease indications described herein.

Kits of the present disclosure can additionally include labels or instructions for using the kit components in any method of the invention. A kit can include the Aβ-oligomer-specific antigen binding molecule as taught herein, the conjugate as taught herein, the multimer as taught herein or expression vector, preferably wherein the expression vector is an AAV viral vector, as taught herein in a pack, or dispenser together with instructions for administering the Aβ-oligomer-specific antigen binding molecule as taught herein, the conjugate as taught herein, or the multimer as taught herein in a method as taught herein. Instructions can include instructions for practicing any of the methods described herein including treatment, detection, monitoring or diagnostic methods. Instructions may additionally include indications of a satisfactory clinical endpoint or any adverse symptoms that may occur, or additional information required by regulatory agencies such as the Food and Drug Administration for use on a human subject.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive. The present disclosure includes the following non-limiting examples.

EXAMPLES

Figure 1:
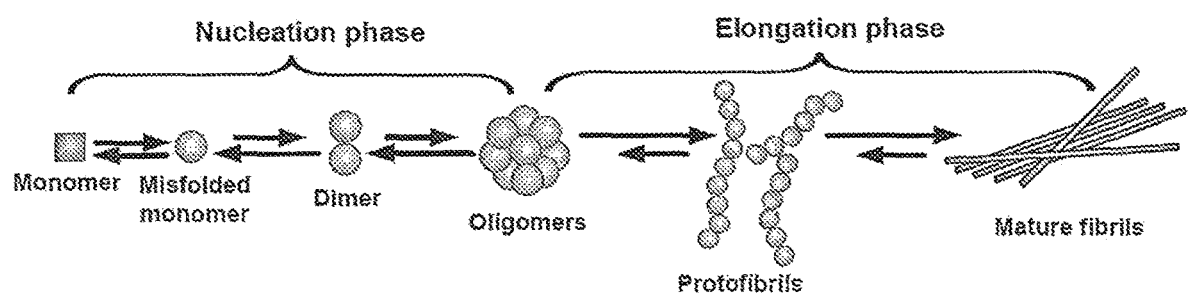
FIG. 1 shows a schematic simplified depiction of the various Aβ species occurring in the brain as well as in solutions.
Figure 2:
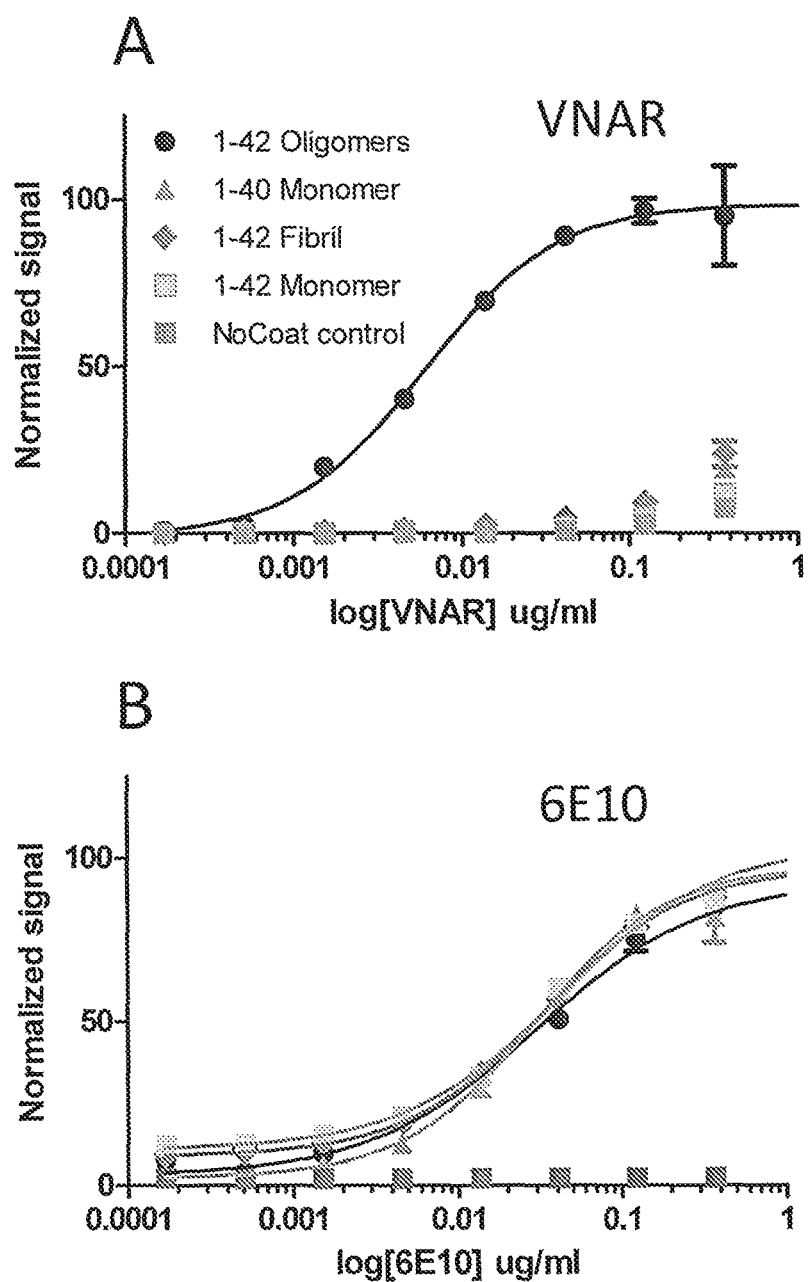
FIG. 2 shows specific binding of CBB-VNAR to oligomers. The experiment was performed as described in detail in example 1. Briefly, different amyloid derived species (monomer, oligomer, fibril) were immobilized to ELISA plates and probed with either the generic amyloid recognizing antibody 6E10 or with CBB-VNAR. CBB-VNAR binds to oligomers with high affinity, whereas CBB-VNAR does not appear to bind to monomer or fibril (A). Conversely, whereas 6E10 appears to bind to oligomers, monomers and fibrils with similar affinity (B).

Example 1: Binding Selectivity and Affinity Towards Different Amyloid Beta Derived Species as Determined Using ELISA To probe the binding affinities of CBB-VNAR towards different amyloid beta species and aggregation states, ELISA assays were performed. As a comparator antibody, the well-characterized 6E10 antibody was used. The 6E10 antibody recognizes N-terminal amino acid residues 3-8 of amyloid beta (EFRHDS), an epitope that is present and available for antibody binding in amyloid beta 1-42 derived antigens regardless of the physical form or aggregation state (Crisostomo et al., 2015. Data Brief. 2015 Aug. 6; 4:650-8.; Frenzel et al., 2014. PLoS One. 2014 Mar. 3; 9(3):e89490). Amyloid beta aggregates were prepared by incubation of monomeric synthetic amyloid beta 1-42 monomer in either F-12 medium (for oligomers) or 10 mM HCl (for fibrils) essentially as described by Dahlgren et al. (2002. J Biol Chem. 2002 Aug. 30; 277(35):32046-53). Amyloid beta derived antigens in different forms (oligomer, monomer, fibril, all at 5 µg/ml) were immobilized to Nunc Amino Immobilizer plates and blocked with ethanolamine according to the manufacturer's instructions. After washing, plates were probed with different concentrations of either FLAG-tagged CBB-VNAR or biotinylated 6E10 antibody (in parallel and on the same plates) for 1 hour. Bound antibody was then detected using anti-FLAG-M2-HRP (for CBB-VNAR) or with streptavidin-HRP (for 6E10-biotin). In accordance with literature data (Pettersson et al. BMC Neurosci. 2010 Oct. 5; 11:124. doi: 10.1186/1471-2202-11-124), it is observed that the 6E10-biotin affinity is not dependent on the physical form of the amyloid beta peptide (average EC50 31±7 ng/ml). In contrast, for CBB-VNAR it is observed that it binds to oligomers with high affinity (EC50 4±1 ng/ml), whereas CBB-VNAR does not appear to bind to monomer or fibril (FIG. 2A). Thus, in this experiment the apparent binding of CBB-VNAR to oligomeric amyloid beta 1-42 is strongly preferred over the binding to amyloid beta monomer or to fibrils by at least 500-fold. The affinity of CBB-VNAR for oligomers of 4±1 ng/ml is equivalent to 0.3 nM (Mw CBB-VNAR=15 kDa). A control FLAG-tagged VNAR, 12Y2, with an amino acid sequence identical to that of CBB-VNAR but different sequences for CDR1 and CDR3 selected on a different target (AMA-1 from *Plasmodium falciparum*) did not provide any detectable signal in these experiments, thereby showing that the identity of the CDR loops is critical towards oligomer recognition.

Example 2: Binding Selectivity and Affinity by Western Blot

Figure 3:
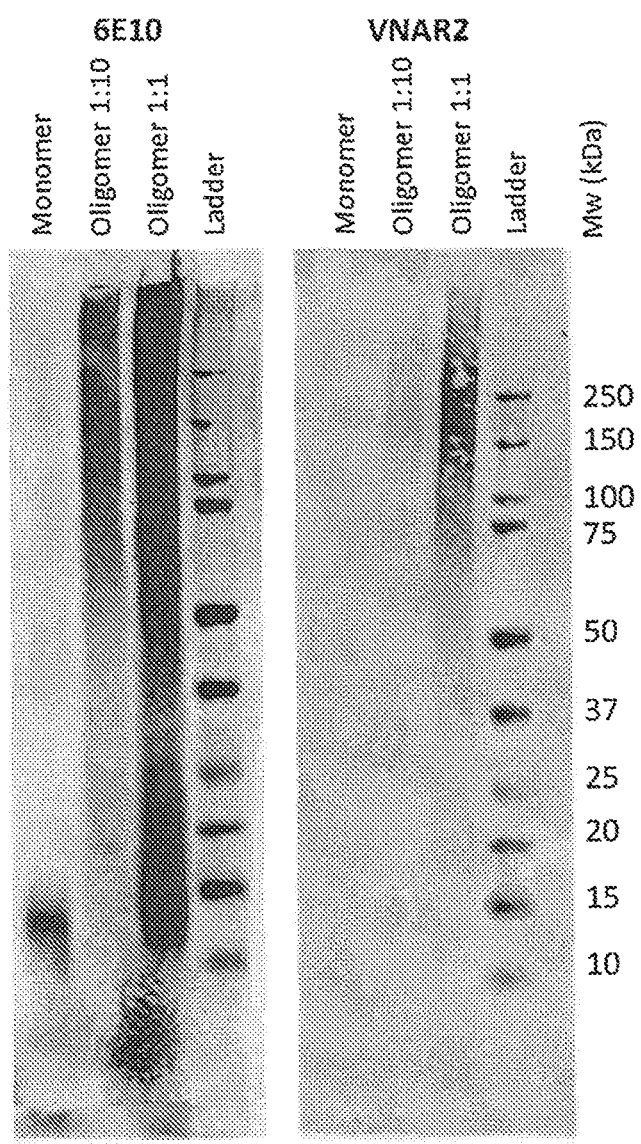
FIG. 3 shows blots probed either with CBB-VNAR ('VNAR') or with 6E10. In the 6E10 blot the Aβ-oligomers become predominantly apparent as a smear at high molecular weight. In the monomeric samples only low molecular weight bands can be observed which most likely correspond to monomer (4.5 kDa), dimer (9 kDa) and trimer (13.5 kDa). In the blot probed with CBB-VNAR, high molecular weight oligomers are detected as a smear centered around ~225 kDa. In contrast, no signal is detected in the monomeric control.

Amyloid beta 1-42 oligomers and 1-42 monomers were run on a Novex NuPAGE 4-12% BIS-TRIS gel, transferred to a Millipore Immobilon FL PVDF membrane and probed with either 6E10-biotin or CBB-VNAR followed by detection of bound antibody with either LICOR streptavidin IRDye conjugate 800CW (for the 6E10 blot) or biotinylated Sigma anti-FLAG-M2 followed by LICOR streptavidin IRDye conjugate 800CW (for the CBB-VNAR blot) using a fluorescent readout. In the 6E10 blot the Aβ-oligomers become predominantly apparent as a smear at high molecular weight. In the monomeric samples only low molecular weight bands can be observed which most likely correspond to monomer (4.5 kDa), dimer (9 kDa) and trimer (13.5 kDa) (FIG. 3, left-hand graph). In the blot probed with CBB-VNAR, high molecular weight oligomers are detected as a smear centered around ~225 kDa. In contrast, no signal is detected in the monomeric control (FIG. 3, right-hand graph).

Example 3: Detection of Amyloid Beta 1-42 Oligomers in Solution

Figure 4:
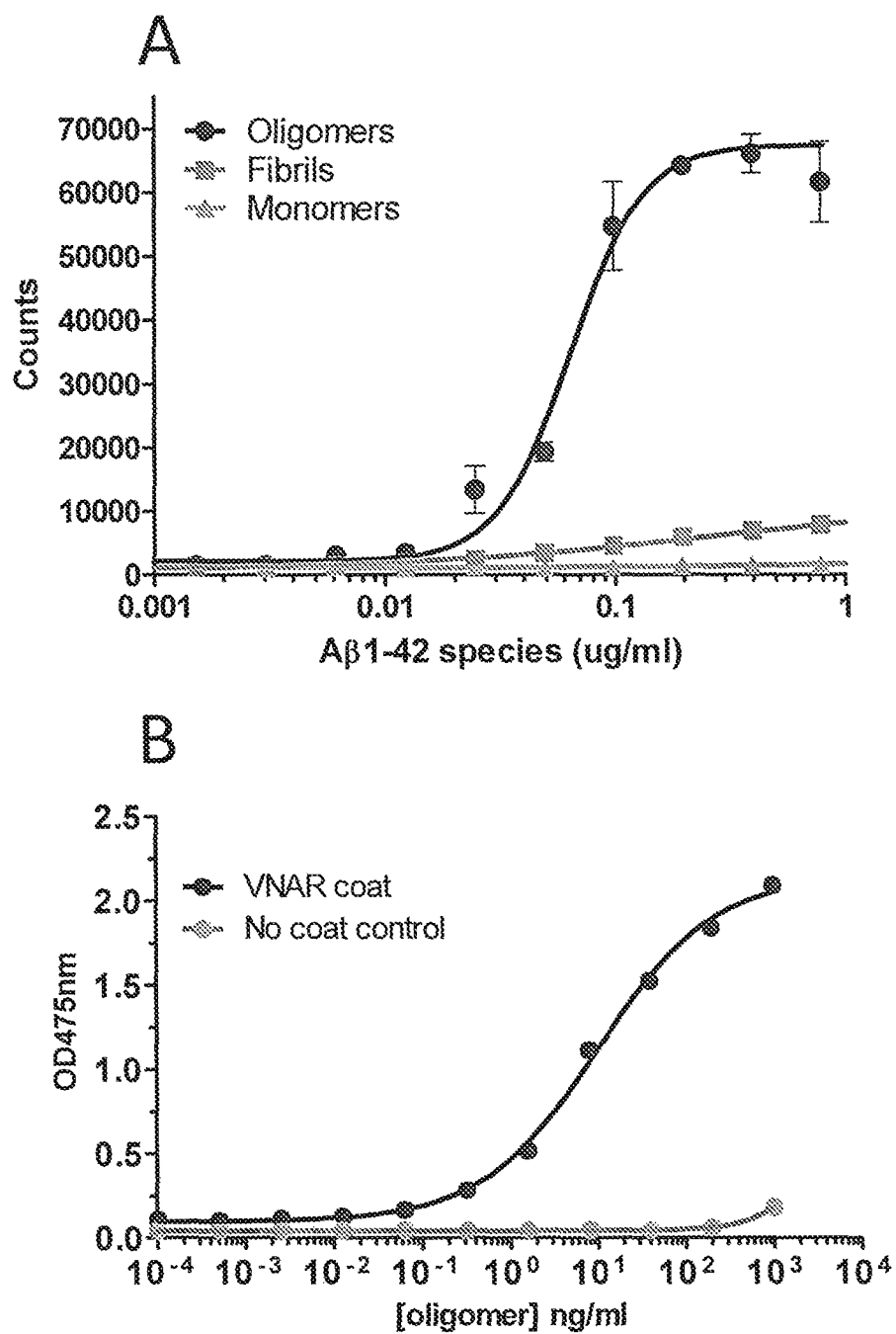
FIG. 4 shows the detection of Aβ-oligomers using two different immunoassay formats. In the first panel oligomers are detected in an Alphascreen® format whereas the signal obtained with monomer or fibril is >10 fold less (A). In this assay signal is generated when 6E10 present on donor beads and CBB-VNAR is present on acceptor beads simultaneously bind to the same oligomer molecule. In the second panel, CBB-VNAR was immobilized to the wells of an ELISA plate to serve as an oligomer capture molecule. Wells were then incubated with different known concentrations of Aβ-oligomers and after washing, CBB-VNAR bound oligomer was detected using the 6E10 antibody.

The selective detection of oligomeric amyloid beta 1-42 was demonstrated in an immunoassay employing a bead-based proximity assay (Alphascreen®, Perkinelmer). The generic amyloid beta binding antibody 6E10-biotin was immobilized on streptavidin Alphascreen®donor beads, while FLAG-tagged CBB-VNAR was immobilized on anti-FLAG Alphascreen®acceptor beads. These beads were incubated with different concentrations of amyloid beta 1-42 derived antigens (oligomers, monomers, fibrils, all prepared as described in example 1). In this format, a specific signal is generated when donor/6E10 and acceptor/CBB-VNAR beads simultaneously bind to different epitopes on the same molecule. In a typical assay, 5 µl amyloid beta or control solutions were incubated with 5 µl 6 nM 6E10-biotin (Covance) and 5 µl 0.13 uM FLAG-tagged CBB-VNAR in assay buffer (10 mM TRIS pH 7.2 containing 140 mM NaCl and 0.01% Tween20). After 20 min incubation in the dark, 5 µl streptavidin donor beads+anti-FLAG acceptor beads (both at 40 ug/ml) diluted in the assay buffer were added and the plates were incubated for 1 hour in the dark. Plates were then read using a Perkinelmer Enspire® plate reader using the 384 well factory preset measuring protocol. The amyloid beta 1-42 oligomers were detected with an apparent EC50 value of 0.1 ug/ml while the background corrected signal obtained with amyloid beta monomers or fibrils was >10 fold less. It could not be excluded that residual signal observed with the monomer and fibril samples was due to the presence of low amounts of oligomeric amyloid beta species formed by, for example, monomer association or fibril dissociation during the experiment. Because the Alphascreen® assay format contains several binding equilibria that affect signal read-out, the detection sensitivity of the Alphascreen® assay does not report on the absolute affinity of CBB-VNAR for oligomers. Stable Crossbeta oligomers (Perkin Elmer Amyloid Oligomers AlphaLISA High-Specificity Detection Kit (AL334F)) were also detected using an ELISA sandwich immunoassay format where the CBB-VNAR was immobilized to Nunc amino immobilizer plates (2 µg/ml coating, 1 hr rT) to serve as oligomer capture molecule. After incubation of the CBB-VNAR coated wells with different amounts of stable oligomer for 1 hour, wells were washed and bound oligomer was detected using sequential incubation with 6E10-biotin and streptavidin-HRP as described in example 1. Aβ-oligomers could be detected (EC50 10±2 ng/ml) while no signal above the background was observed in wells that were not coated with CBB-VNAR or did not contain oligomer (FIG. 4).

Example 4

Intrinsic Fluorescence Quenching.

Figure 5:
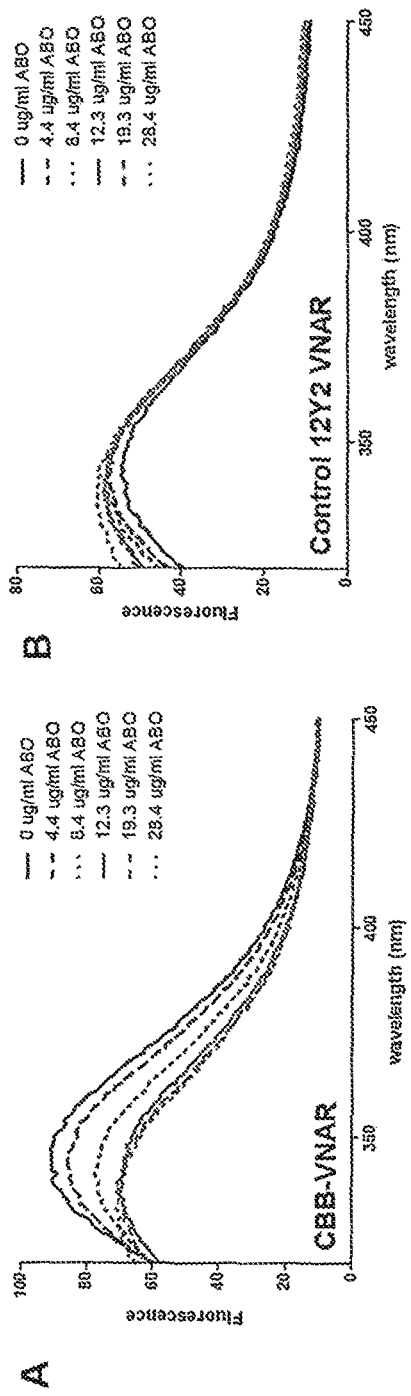
FIG. 5: The binding of amyloid 1-42 oligomer (ABO) involves tryptophan in the CDRs of CBB-VNAR. (A) Fluorescence emission spectra of CBB-VNAR recorded in the presence of different amounts of ABO as indicated in the figure. (B) Same as A, but then employing the 12Y2 control VNAR that does not bind ABO. (C) Normalized fluorescence intensities determined from the data presented in panels in A and B. (D) The experimentally determined X-Ray structure of the 12Y2 control protein (PDB entry 1VES) and a model of CBB-VNAR generated by homology modelling using the Swiss PBD Viewer 4.1 software package. The two tryptophan residues in the VNAR framework present in both the control 12Y2 protein and CBB-VNAR are represented as light grey spheres, whereas the additional two Trp residues present in CBB-VNAR CDR are represented as dark grey spheres.

The amino acid residue tryptophan (Trp or W) intrinsically fluoresces upon excitation in the range 280-295 nm. The emission intensity (i.e. quantum yield) and emission wavelength are sensitive towards the local environment of the Trp residue. The local environment can change, for example, when the Trp residue is involved in conformational changes or ligand binding. Therefore, Trp emission is widely used to study proteins and their interaction with other proteins or small molecules. The invariable core structure of the VNAR as isolated from wobbegong sharks has two Trp residues (see sequence below, Trp indicated in black) of which one is buried inside the protein whereas the other is exposed to the solvent (see FIG. 5D). The CBB-VNAR has two additional Trp residues in the CDR regions (one in CDR1, one in CDR3). No Trp residues are present in the CDR regions of the 12Y2 control protein. Apart from the CDR sequences, this control 12Y2 protein has an amino acid sequence identical to that of CBB-VNAR. To evaluate whether the Trp residues of CBB-VNAR are involved in the binding of amyloid beta oligomer antigen, a fluorescence titration study was performed. For this experiment, 0.5 uM CBB-VNAR or 12Y2 control VNAR were titrated with known quantities of amyloid beta oligomer (ABO) in Phosphate Buffered Saline (PBS) buffer, pH 7.2. The buffer was complemented with 0.5 mM Ethylenediaminetetraacetic acid (EDTA) to prevent any metal-induced collisional quenching. After each ABO addition, the sample was equilibrated until the Trp fluorescence intensity was stable, and Trp emission spectra were recorded between 320 and 450 nm using 280 nm excitation. Because CBB-VNAR contains two Trp residues in the CDR regions whereas the control 12Y2 protein does not, the emission intensity of native CBB-VNAR is higher than that of the 12Y2 control protein in absence of ABO. Upon addition of ABO, the emission intensity of CBB-VNAR decreases in a dose-dependent and saturable fashion where the intensity decreases to about 70% of the intensity measured for the native protein (FIGS. 5A and C). This intensity change is accompanied by a shift in the apparent emission maximum from 345 nm for the native protein to about 335 nm of the ABO bound form. In contrast, the Trp emission of the 12Y2 control protein is not sensitive towards the addition of ABO using the concentrations employed (FIGS. 5B and C). This result demonstrates that the ABO-induced quenching observed for CBB-VNAR does not originate from changes associated with the two Trp residues in the VNAR framework core sequence and, thus, that binding of the ABO antigen to CBB-VNAR involves Trp in the CDR sequences.

Example 5

AAV5 Cloning and Sequence

The small (4.8 kb) ssDNA AAV genome consists of two open reading frames, Rep and Cap, flanked by two 145 base inverted terminal repeats (ITRs). These ITRs base pair to allow for synthesis of the complementary DNA strand. Rep and Cap are translated to produce multiple distinct proteins (Rep78, Rep68, Rep52, Rep40—required for the AAV life cycle; VP1, VP2, VP3-capsid proteins). When constructing an AAV transfer plasmid, the transgene (here, a nucleic acid molecule encoding the Abeta-oligomer specific antigen binding molecule as taught herein) is placed between the two ITRs, and Rep and Cap are supplied in trans. In addition to Rep and Cap, AAV requires a helper plasmid containing genes from adenovirus. These genes (E4, E2a and VA) mediate AAV replication. The transfer plasmid, Rep/Cap, and the helper plasmid are transfected into HEK293 cells, which contain the adenovirus gene E1+, to produce infectious AAV particles. Rep/Cap and the adenovirus helper genes may also be combined into a single plasmid.

The invention claimed is:

1. An amyloid beta peptide (Aβ)-oligomer-specific antigen binding molecule, wherein the amyloid peptide (Aβ)-oligomer-specific antigen binding molecule comprises the amino acid sequence of SEQ ID NO: 1.

2. An amyloid beta peptide (Aβ)-oligomer-specific antigen binding molecule comprising an amino acid sequence comprising the structure X-CDR1-Y-CDR3-Z,
    wherein the amyloid peptide (Aβ)-oligomer-specific antigen binding molecule comprises the amino acid sequence of SEQ ID NO: 1 with up to two amino acid substitutions,
    wherein CDR1 comprises the amino acid sequence of amino acid residues 27-32 of SEQ ID NO:1 (QNGWSR) or wherein at most one amino acid in CDR1 is a substituted amino acid,
    wherein CDR3 comprises the amino acid sequence of amino acid residues 85-102 of SEQ ID NO:1 (LLN-PRREEFWFSRRYPVV) or wherein at most one amino acid in CDR3 is a substituted amino acid,
    wherein X is represented by Framework Region (FW)1,
    wherein Y is represented by FW2-Hypervariable Region 2 (HV2)-FW3a, and
    wherein Z is represented by FW4.

3. An Aβ-oligomer-specific antigen binding molecule according to claim 2, which consists of the amino acid sequence of SEQ ID NO: 1.

4. A conjugate comprising an Aβ-oligomer-specific antigen binding molecule according to claim 2 and an agent.

5. A multimer comprising two or more Aβ-oligomer-specific antigen binding molecules according to claim 2 or conjugates comprising the Aβ-oligomer-specific antigen binding molecule and an agent.

6. A pharmaceutical composition comprising the Aβ-oligomer-specific antigen binding molecule according to claim 2, or a conjugate comprising the Aβ-oligomer-specific antigen binding molecule and an agent, or a multimer comprising two or more of the Aβ-oligomer-specific antigen binding molecules and an acceptable carrier, or a AAV viral vector comprising a nucleic acid molecule encoding the Aβ-oligomer-specific antigen binding molecule.

7. A kit suitable for detecting Aβ-oligomers, comprising the Aβ-oligomer-specific antigen binding molecule according to claim 2.

8. The Aβ-oligomer-specific antigen binding molecule according to claim 2, wherein the Aβ-oligomer-specific antigen binding molecule is encoded by a nucleic acid comprised in an expression vector that is an AAV viral vector.

9. A nucleic acid molecule encoding the Aβ-oligomer-specific antigen binding molecule according to claim 2.

10. An expression vector comprising a AAV viral vector comprising the nucleic acid molecule according to claim 9.

11. A host cell comprising the nucleic acid molecule according to claim 9.

12. A method of reducing Aβ-oligomer levels in a subject, said method comprising the step of administering to said subject an Aβ-oligomer-specific antigen binding molecule according to claim 2.

13. A method of measuring Aβ-oligomer levels in a test sample, said method comprising the steps of:
    (a) contacting a test sample with an Aβ-oligomer-specific antigen binding molecule according to claim 2; and
    (b) detecting the binding molecule or conjugate or multimer/Aβ-oligomer complex.

14. The method according to claim 13, which is for diagnosing a subject suffering from a neurodegenerative disease.

15. The method according to claim 14, wherein the neurodegenerative disease is selected from the group consisting of Alzheimer's Disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, and Gaucher's disease.

16. A method of assessing disease progression in a subject being treated for a neurodegenerative disease comprising the steps of:
    (a) contacting a first test sample taken at a first time point with an Aβ-oligomer-specific antigen binding molecule according to claim 2;
    (b) contacting a second test sample taken at a second time point with the Aβ-oligomer-specific antigen binding molecule; and
    (c) comparing the level of binding molecule or conjugate or multimer/Aβ-oligomer complex of the first test sample to the level of binding molecule or conjugate or multimer/Aβ-oligomer complex of the second test sample.

17. A method according to claim 16, wherein an increased level of binding molecule or conjugate or multimer/Aβ-oligomer complex in the second test sample compared to that in the first test sample is indicative of progression of said neurodegenerative disease in the subject.

18. A method according to claim 16, wherein a decreased level of binding molecule or conjugate or multimer/Aβ-oligomer complex in the second test sample compared to that in the first test sample is indicative of effectiveness of the treatment of said neurodegenerative disease in the subject.

19. A method according to claim 16, wherein the neurodegenerative disease is selected from the group consisting of Alzheimer's Disease, Down's syndrome, mild cognitive impairment, cerebral amyloid angiopathy, vascular dementia, multi-infarct dementia, Parkinson's disease, Dementia with Lewy Bodies, Huntington's disease, Creutzfeldt-Jakob disease, cystic fibrosis, and Gaucher's disease.

* * * * *

SEQUENCE LISTING

<160> NUMBER OF SEQ ID NOS: 6

<210> SEQ ID NO 1
<211> LENGTH: 115
<212> TYPE: PRT
<213> ORGANISM: Artificial sequence
<220> FEATURE:
<223> OTHER INFORMATION: CBB-VNAR

<400> SEQUENCE: 1

Ala Trp Val Asp Gln Thr Pro Arg Thr Ala Thr Lys Glu Thr Gly Glu

```
                1               5                   10                  15
    Ser Leu Thr Ile Asn Cys Val Leu Arg Asp Gln Asn Gly Trp Ser Arg
                    20                  25                  30

Thr Gly Trp Tyr Arg Thr Lys Leu Gly Ser Thr Asn Glu Gln Ser Ile
                    35                  40                  45

Ser Ile Gly Gly Arg Tyr Val Glu Thr Val Asn Lys Gly Ser Lys Ser
                    50                  55                  60

Phe Ser Leu Arg Ile Ser Asp Leu Arg Val Glu Asp Ser Gly Thr Tyr
    65                  70                  75                  80

Lys Cys Gln Ala Leu Leu Asn Pro Arg Glu Glu Phe Trp Phe Ser
                        85                  90                  95

Arg Arg Tyr Pro Val Val Lys Gly Ala Gly Thr Ala Leu Thr Val Lys
                        100                 105                 110

Ala Ala Ala
            115

<210> SEQ ID NO 2
<211> LENGTH: 97
<212> TYPE: PRT
<213> ORGANISM: homo sapiens

<400> SEQUENCE: 2

Leu Gln Val Asp Ile Val Pro Ser Gln Gly Glu Ile Ser Val Gly Glu
    1               5                   10                  15

Ser Lys Phe Phe Leu Cys Gln Val Ala Gly Asp Ala Lys Asp Lys Asp
                    20                  25                  30

Ile Ser Trp Phe Ser Pro Asn Gly Glu Lys Leu Thr Pro Asn Gln Gln
                    35                  40                  45

Arg Ile Ser Val Val Trp Asn Asp Asp Ser Ser Thr Leu Thr Ile
                50                  55                  60

Tyr Asn Ala Asn Ile Asp Asp Ala Gly Ile Tyr Lys Cys Val Val Thr
    65                  70                  75                  80

Gly Glu Asp Gly Ser Glu Ser Glu Ala Thr Val Asn Val Lys Ile Phe
                        85                  90                  95

Gln

<210> SEQ ID NO 3
<211> LENGTH: 17
<212> TYPE: PRT
<213> ORGANISM: Artificial sequence
<220> FEATURE:
<223> OTHER INFORMATION: PelB leader sequence

<400> SEQUENCE: 3

Pro Thr Ala Ala Ala Gly Leu Leu Leu Leu Ala Ala Gln Pro Ala Met
    1               5                   10                  15

Ala

<210> SEQ ID NO 4
<211> LENGTH: 90
<212> TYPE: PRT
<213> ORGANISM: artificial sequence
<220> FEATURE:
<223> OTHER INFORMATION: i-body
<220> FEATURE:
<221> NAME/KEY: Xaa
<222> LOCATION: (23)..(23)
<223> OTHER INFORMATION: Q or K
<220> FEATURE:
<221> NAME/KEY: Xaa
```

```
<222> LOCATION: (24)..(24)
<223> OTHER INFORMATION: V or A
<220> FEATURE:
<221> NAME/KEY: Xaa
<222> LOCATION: (27)..(32)
<223> OTHER INFORMATION: any amino acid
<220> FEATURE:
<221> NAME/KEY: Xaa
<222> LOCATION: (80)..(80)
<223> OTHER INFORMATION: any amino acid and any number of amino acids
      between 10 and 20 inclusive

<400> SEQUENCE: 4

Leu Gln Val Asp Ile Val Pro Ser Gln Gly Glu Ile Ser Val Gly Glu
1               5                   10                  15

Ser Lys Phe Phe Leu Cys Xaa Xaa Ala Gly Xaa Xaa Xaa Xaa Xaa Xaa
            20                  25                  30

Ile Ser Trp Phe Ser Pro Asn Gly Glu Lys Leu Thr Pro Asn Gln Gln
            35                  40                  45

Arg Ile Ser Val Val Trp Asn Asp Asp Ser Ser Thr Leu Thr Ile
        50                  55                  60

Tyr Asn Ala Asn Ile Asp Asp Ala Gly Ile Tyr Lys Cys Val Val Xaa
65                  70                  75                  80

Glu Ala Thr Val Asn Val Lys Ile Phe Gln
                85                  90

<210> SEQ ID NO 5
<211> LENGTH: 6
<212> TYPE: PRT
<213> ORGANISM: Artificial sequence
<220> FEATURE:
<223> OTHER INFORMATION: CDR1

<400> SEQUENCE: 5

Gln Asn Gly Trp Ser Arg
1               5

<210> SEQ ID NO 6
<211> LENGTH: 18
<212> TYPE: PRT
<213> ORGANISM: Artificial sequence
<220> FEATURE:
<223> OTHER INFORMATION: CDR3

<400> SEQUENCE: 6

Leu Leu Asn Pro Arg Arg Glu Glu Phe Trp Phe Ser Arg Arg Tyr Pro
1               5                   10                  15

Val Val
```